United States Patent [19]

Ryan

[11] 4,198,206
[45] Apr. 15, 1980

[54] METHOD FOR PREPARING A PLATELET REFERENCE CONTROL

[76] Inventor: Wayne L. Ryan, 3631 S. 116th Ave., Omaha, Nebr. 68144

[21] Appl. No.: 937,955

[22] Filed: Aug. 30, 1978

Related U.S. Application Data

[63] Continuation-in-part of Ser. No. 805,810, Jun. 13, 1977, Pat. No. 4,160,644.

[51] Int. Cl.² ............................................. G01N 33/16
[52] U.S. Cl. .................................. 23/230 B; 252/408; 424/3
[58] Field of Search ..................... 23/230 B; 252/408; 424/3

[56] References Cited

U.S. PATENT DOCUMENTS

| | | | |
|---|---|---|---|
| 3,574,137 | 4/1911 | DeCasperis | 23/230 B |
| 3,632,735 | 1/1972 | Kita | 424/3 |
| 3,634,581 | 1/1972 | Thomas | 424/3 |
| 3,640,896 | 2/1972 | DeCasperis | 23/230 B |
| 3,714,345 | 1/1973 | Hirata | 424/3 |
| 3,884,579 | 5/1975 | Mauthner | 252/408 |
| 3,984,532 | 10/1976 | de Castro | 23/230 B |

OTHER PUBLICATIONS

Red Cell Freezing by Amer. Nat. Red Cross, Meryman, Am. J. of Med. Tech., 44, 265, 1975.

*Primary Examiner*—Michael S. Marcus
*Attorney, Agent, or Firm*—Tilton, Fallon, Lungmus & Chestnut

[57] ABSTRACT

A platelet reference control method of preparation wherein aldehyde-reacted platelets are suspended in a phosphate buffer fortified with glycine and ethylene glycol.

4 Claims, No Drawings

METHOD FOR PREPARING A PLATELET REFERENCE CONTROL

This application is a continuation-in-part of my copending application Ser. No. 805,810, filed June 13, 1977, now U.S. Pat. No. 4,160,644.

BACKGROUND AND SUMMARY OF INVENTION

This invention relates to a method for preparing a platelet reference control and, more particularly, a control especially useful with automated counters. The inventive procedure provides a product which meets the demand for quality control in the clinical laboratory for stabilized cellular components of blood to assess the reproducibility and accuracy of counters.

Platelets for platelet reference controls are prepared by reaction with an aldehyde, preferably glutaraldehyde. After appropriate washing by centrifugation to remove the glutaraldehyde and aggregates, the "aldehyde-reacted" platelets are suspended in a phosphate buffer. The suspended platelets are not stable and will aggregate under a number of circumstances. In addition, the "aldehyde-reacted" platelets gradually change shape, shrinking in size as they age.

The aldehyde-reacted platelets are intended to be used in particle counters which are affected by particle size. Thus, the reference control should ideally contain platelets which are as similar as possible in size to the platelet particles in normal human blood. It is apparent that aggregation will affect the count and size of the particles in the reference control. It is also apparent that the shrinking that occurs with time and heat also will impair the value of the control—since the platelets are no longer the same size as platelets in human blood.

The objective was to produce aldehyde-reacted platelets that do not aggregate, which have the same size as platelets in human blood, and which maintain their size for at least six months.

Factors found to affect aggregation of aldehyde-reacted platelets are: ionic strength and pH of the buffer or salt solution; and freezing of the solution. Freezing problems can be avoided by adding 0.5–1.5 molar ethylene glycol (alternatively glycerin or methanol) to the suspension. The size of the platelets can be controlled, i.e., stabilized, through the addition of 0.1–0.3 glycine to the suspension.

DETAILED DESCRIPTION

To evaluate various factors affecting aggregation, the following experimentation was performed.

SALT CONCENTRATION 250,000 aldehyde-reacted platelets per $mm^3$ were suspended in 1.0, 0.5, 0.25, and 0.1 M NaCl and in 1.0, 0.5, 0.25, and 0.1 M $Na_2HPO_4$. The platelets were held at 25° and examined microscopically for aggregates every seven days. After 14 days, the platelets in 1.0 and 0.5 M solutions showed evidence of aggregation. After 30 days only the 0.1 M solutions were free of aggregates.

EFFECT OF pH 250,000 aldehyde-reacted platelets/$mm^3$ were suspended in phosphate buffer 0.1 M $Na_2HPO_4$ at pH of 7.4, 7.0, 6.5, 6.0, and 5.5. Aggregation occured within a few hours at pH 5.5 and 6.0. At the higher pH values the platelets did not aggregate.

EFFECT OF FREEZING

Because the platelet reference control is frequently subjected to freezing when shipped during the winter and sometimes in the laboratory freezer, the effects of freezing were studied. Platelets were suspended at 250,000 aldehyde-reacted platelets/$mm^3$ in $Na_2HPO_4$ 0.1 M. pH 7.4 and frozen at −20° for 1 hour, 6 hours, and 24 hours. All the samples were badly aggregated when thawed. In addition, it was found that the longer the samples are frozen the more severe the aggregation. In addition to aggregation, the freezing also caused a decrease in size of the platelets. Because of the size change and aggregation, the platelet count decreased up to 50%.

A possible solution to the freezing problem was the use of glycerin. High concentrations of glycerin are used to protect red blood cells from lysis during freezing (Red Cell Freezing by the American National Red Cross, H. T. Meryman, American Journal of Medical Technology, 41, 265, 1975). In this method however, approximately 6 M glycerol is used. The addition of the glycerol lowers the freezing point and the amount of ice formed at any temperature.

250,000/$mm^3$ of aldehyde-reacted platelets were suspended in 0.1 M phosphate buffer at pH 7.4. To the platelet suspensions were added either ethylene glycol, methanol, or glycerin at 0.1, 0.5, 1.0, 1.5, 2.0, 10.0 M. The suspensions were frozen at −20° for 24 hours and examined microscopically for aggregation. In addition, each sample was examined on a Coulter ZBI ® with a Channelyzer to determine the platelet size.

| PLATELET AGGREGATION AFTER FREEZING | | | |
|---|---|---|---|
| Molarity | Ethylene Glycol | Glycerin | Methanol |
| 0.0 | +++ | +++ | +++ |
| 0.1 | + | +++ | +++ |
| 0.5 | 0 | 0 | + |
| 1.0 | 0 | 0 | 0 |
| 2.0 | 0 | 0 | |
| 10.0 | 0 | 0 | |

Aggregation : Severe = +++ None = 0

In view of the prior teaching, it was surprising to find that protection from aggregation and size alteration is obtained at 0.5–1.5 M with each of the additives. Ethylene glycol is the most effective. Concentrations in excess of 1 M such as are used for freezing red blood cells have a deterious effect on the platelets, causing them to decrease in size after a few days storage. Therefore, the only acceptable concentration is 0.5–1.5 M. Of the three compounds, ethylene glycol is preferred because of its greater efficacy. In addition, glycerin is sticky and methanol may evaporate which could alter the platelet count.

PLATELET SIZE

As indicated earlier, the platelets in the reference control should have the same size range as platelets in human blood. If not, the instruments used to count platelets can be functioning improperly and the operator is not aware of it. That is, the platelet counter may be measuring particles from 1–10$\mu^3$ whereas it should be measuring particles from 1–26$\mu^3$. If the platelet control has decreased in size to a maximum value of 3–4$\mu^3$, all the platelets in the reference control are counted but the platelets in human blood would not be counted.

Serendipity played a big role in finding a solution to this problem. It is part of the manufacturing process to wash the aldehyde-reacted platelets with glycine. This is a standard procedure to neutralize any free aldehyde groups. The amino acid reacts with the free aldehyde group as in a Sorenson titration:

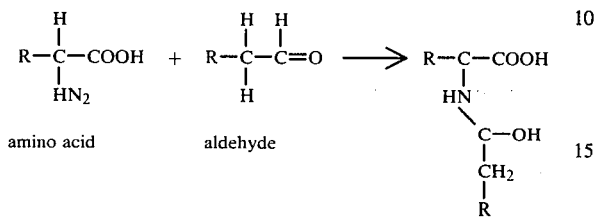

The amino nitrogen can accept another aldehyde to form:

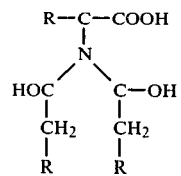

By reacting the aldehyde-treated platelets with an excess of the amino acid glycine all of the aldehyde groups are reacted so that further reactions with the protein cannot occur. The further reactions include cross-linking which leads to hardening and shrinking of the platelet.

It is standard practice in quality control to test platelets for thermal stability at 40°, 25°, and 6° and measure the size distribution of the platelets with the Coulter ZBI ® at weekly intervals. One lot was obtained which showed little or no shrinkage even at 40°. Examination of this lot and from consideration of the problem, I concluded that the glycine had not been completely removed during the centrifugation and washing step. In addition, I discovered that the reaction with glycine is reversible. The glycine dissociates from the aldehyde. By leaving a small amount of glycine in the sample, I discovered this markedly enhances the stability of the platelet, preventing shrinkage.

250,000/mm$^3$ platelets were reacted with glutaraldehyde. The glutaraldehyde was removed by centrifugation and 0.3 M glycine added. After incubation of the platelets in glycine for one hour, the glycine was removed and the platelets suspended as follows:

Group

1. Not washed with glycine.
2. Washed with glycine.
3. Washed with glycine and 0.03 M glycine added to the platelets.
4. Washed with glycine and 0.1 M glycine added to the platelets.
5. Washed with glycine and 0.15 M glycine added to the platelets.
6. Washed with glycine and 0.30 M glycine added to the platelets.

Each group was stored at 40°±1° and examined weekly for size distribution with a Coulter ZBI ®and a Channelyzer. There was no difference between Group 1 and 2. Washing with glycine alone proved of no value. The 0.03 M (Group 3) was only slightly better than the washed and unwashed samples and is unacceptable. However, at 0.1 M, 0.15 M and 0.30 M glycine only a slight change in size distribution occurred, as can be appreciated from the following table:

Mode Cell Volume Change at 40° C. for Six Weeks All groups started at 5.72μ$^3$.

Group

1. Decreased to 3.12μ$^3$
2. Decreased to 3.12μ$^3$
3. Decreased to 3.64μ$^3$
4. Decreased to 5.2μ$^3$
5. Decreased to 5.3μ$^3$
6. Decreased to 5.2μ$^3$ Because of the size distribution shift the platelet count decreased in Group 1, 2, and 3 by 34% but no significant count changed occurred in the groups containing glycine above 0.1 M.

In addition to testing glycine, I also tested aspartic acid, lysine, proline, hydroxyproline, arginine, cysteine, glutamic acid, glutamine, alanine, tryptophan, and the dipeptide glyclyglycine. The basic amino acids and the acidic amino acids caused aggregation. The neutral amino acid, alanine, was acceptable; but no more effective than glycine. The dipeptide did not provide size protection. Thus, a 0.10 M to 0.30 M glycine or alanine solution protects aldehydereacted platelets from shrinking during storage at elevated temperatures. The preferred preparation contains the following:

| Ethylene glycol | 1.5 Molar | 93 g/liter |
| --- | --- | --- |
| Sodium Phosphate | 60 mOsM pH 7.4 | 16.2 g/l |
| Glycine | 0.10 Molar | 7.5 g/l |
| Polyethylene glycol 6000 | 0.017 Molar | 100 g/l |
| Phenol | 0.03 Molar | 2.5 g/l |

The preferred procedure for adding the ingredient is as follows: Glycine-washed platelets are sedimented by centrifugation and then suspended in a 60 milliosmolar Na$_2$HPO$_4$, pH 7.4 containing 0.25% phenol and 0.15 M glycine. The platelets are completely suspended before going to the next step by stirring for one hour.

Another solution is prepared which contained 20% polyethylene glycol 6000, 20% ethylene glycol, 0.15 M glycine, 0.25% phenol in 60 milliosmolar Na$_2$HPO$_4$ (pH 7.4). Equal volumes of this and the above solutions are slowly mixed for over an hour.

An important point of the procedure is to avoid adding the polyethylene glycol to the platelets before putting them in suspension. Failure to do so results in a marked shrinkage of the platelet volume and fragmentation of some of the platelets. This preparation protects aldehyde-treated platelets from freezing, adsorption, and shape changes. It is remarkable that the osmolarity is so high. A solution this high in osmolarity would be expected to shrink the platelets or even burst them. The osmolarity of a solution is a method of stating the osmotic pressure produced by a given solution. This can be approximated by multiplying the molarity times the number of ions resulting from ionization. For example, a one molar HCl solution has an osmolarity of two. This simple relationship exists in dilute solutions with highly ionized salts.

However, it is necessary that all of the agents be added very slowly or osmolar damage occurs. The slow addition (of the order of one hour and optimally two hours) apparently permits equilibration of the external and internal milieu.

In the procedure just set down, it will be noted that the glycine wash was still employed to remove all free glutaraldehyde that remains from the fixing step. However, it is not really necessary, but more of a clean-up operation.

From the foregoing, it will be seen that the platelet reference control is effectively stabilized both as to aggregation and platelet size through a choice of the ionic strength and pH of the buffer or salt solution and the addition of glycine or alanine to counteract shrinkage and the addition of a member such as ethylene glycol to oppose the injurious effects of freezing. To this I add polyethylene glycol as described in greater detail in my above identified application Ser. No. 805,810 to achieve time and agitation stabilization. Phenol is added as a further, conventional preservative.

While in the foregoing specification, a detailed description of the invention has been set down for the purpose of explanation, many variations of the details herein given may be made by those skilled in the art without departing from the spirit and scope of the invention.

I claim:

1. A method for preparing a platelet reference control comprising:
    reacting platelets with an aldehyde and removing the aldehyde by centrifugation
    suspending the aldehyde-reacted platelets that have been washed in an amino acid solution in a solution of: (a) a first member selected from the class consisting of glycine and alanine having a molarity in the range of about 0.10 to about 0.30, (b) a second member selected from the class consisting of ethylene glycol, glycerine and methanol having a molarity in the range of about 0.5 to about 1.5, (c) a third member selected from the class of sodium chloride and sodium phosphate having a molarity of from about 0.1 to about 1.0 and a pH in the range of at least about 6.5–7.4, and (d) a solid polyethylene glycol.

2. The method of claim 1 in which said first member is glycine, said second member is ethylene glycol and said third member is sodium phosphate.

3. The method of claim 1 in which said platelets are suspended before contact with said polyethylene glycol.

4. The method of claim 3 in which said platelet suspension step prior to contact with polyethylene glycol is performed in a period of the order of at least about one hour.

* * * * *